(12) United States Patent
Trishaun (10) Patent No.: US 12,280,275 B2
(45) Date of Patent: Apr. 22, 2025

(54) MONITORING SYSTEM FOR MASK DEVICE WITH ALERT MESSAGES AND RELATED METHODS

(71) Applicant: Marquette Trishaun, Winter Park, FL (US)

(72) Inventor: Marquette Trishaun, Winter Park, FL (US)

(*) Notice: Subject to any disclaimer, the term of this patent is extended or adjusted under 35 U.S.C. 154(b) by 826 days.

(21) Appl. No.: 17/195,833

(22) Filed: Mar. 9, 2021

(65) Prior Publication Data

US 2021/0346731 A1 Nov. 11, 2021

Related U.S. Application Data

(60) Provisional application No. 63/020,510, filed on May 5, 2020.

(51) Int. Cl.
| | |
|---|---|
| A62B 18/00 | (2006.01) |
| A61B 5/00 | (2006.01) |
| A62B 18/02 | (2006.01) |
| A62B 18/08 | (2006.01) |
| H04W 4/02 | (2018.01) |
| H04W 4/80 | (2018.01) |

(52) U.S. Cl.
CPC .......... *A62B 18/088* (2013.01); *A61B 5/0008* (2013.01); *A61B 5/6803* (2013.01); *A62B 18/02* (2013.01); *H04W 4/023* (2013.01); *H04W 4/80* (2018.02)

(58) Field of Classification Search
CPC .. A61M 16/06; A61M 16/00; A61M 16/1005; A61M 2016/103; A62B 18/088; A62B 18/00; A62B 18/02; A61B 5/0008; A61B 5/6803; H04W 4/023
See application file for complete search history.

(56) References Cited

U.S. PATENT DOCUMENTS

| | | | | |
|---|---|---|---|---|
| 2007/0163588 | A1* | 7/2007 | Hebrank | A61M 16/0069 128/205.29 |
| 2012/0055815 | A1* | 3/2012 | Truex | A62B 27/00 206/205 |
| 2014/0364758 | A1* | 12/2014 | Schindhelm | A61M 16/0633 128/204.22 |
| 2017/0372216 | A1* | 12/2017 | Awiszus | A61F 11/06 |
| 2021/0386320 | A1* | 12/2021 | Lesso | A61B 5/0823 |

* cited by examiner

*Primary Examiner* — Margaret M Luarca
*Assistant Examiner* — Sarah B Lederer
(74) *Attorney, Agent, or Firm* — Allen, Dyer, Doppelt + Gilchrist, PA (57) ABSTRACT

A monitoring system may include a server, and mask devices in communication with the server. Each mask device may include a mask body to be worn by a respective user, an air quality sensor carried by the mask body and configured to detect a contaminant concentration value in air breathed through the mask body, a wireless transceiver carried by the mask body and in communication with the server via a wireless link, and a processor carried by the mask body and coupled to the air quality sensor and the wireless transceiver. The processor may be configured to send an alert message to the server when the contaminant concentration value respectively exceeds a threshold.

20 Claims, 13 Drawing Sheets

FIG. 9C

MONITORING SYSTEM FOR MASK DEVICE WITH ALERT MESSAGES AND RELATED METHODS

RELATED APPLICATION

This application is based upon prior filed copending Application No. 63/020,510 filed May 5, 2020, the entire subject matter of which is incorporated herein by reference in its entirety.

TECHNICAL FIELD

The present disclosure relates to the field of respiratory devices, and, more particularly, to a monitoring system for mask devices and related methods.

SUMMARY

Generally, a monitoring system may include a server, and a plurality of mask devices in communication with the server. Each mask device may include a mask body to be worn by a respective user, an air quality sensor carried by the mask body and configured to detect at least one contaminant concentration value in air breathed through the mask body, a wireless transceiver carried by the mask body and in communication with the server via a wireless link, and a processor carried by the mask body and coupled to the air quality sensor and the wireless transceiver. The processor may be configured to send an alert message to the server when the at least one contaminant concentration value respectively exceeds at least one threshold.

In some embodiments, each mask device may comprise an infrared (IR) sensor carried by the mask body and coupled to the processor. The IR sensor may be configured to detect a body temperature of the respective user. Each mask device may comprise an ambient temperature sensor carried by the mask body and coupled to the processor. The ambient temperature sensor may be configured to detect an ambient temperature.

The processor may be configured to detect at least one of a cough event of the respective user, a sneeze event of the respective user, a breathing event of the respective user, and a fall event of the respective user. The air quality sensor may be configured to detect a plurality of contaminant concentration values. The air quality sensor may be configured to detect the plurality of contaminant concentration values comprising a carbon dioxide concentration value, and a Volatile Organic Compound (VOC) concentration value, for example.

The mask body may comprise a plurality of layers. The plurality of layers may comprise a submicron bio barrier layer, for example. Each mask device may comprise a proximity sensor carried by the mask body, and coupled the processor. The proximity sensor may be configured to detect when the mask body is worn by the respective user. Each mask device may comprise a battery coupled the air quality sensor, the wireless transceiver, and the processor. Additionally, the monitoring system may further comprise a plurality of mobile devices in communication with the server and respectively associated with the plurality of mask devices, and the server may be configured to forward the alert message to a respective mobile device.

Another aspect is directed to a method of operating a monitoring system comprising a server, and a plurality of mask devices in communication with the server. Each mask device comprises a mask body to be worn by a respective user, an air quality sensor carried by the mask body and configured to detect at least one contaminant concentration value in air breathed through the mask body, and a wireless transceiver carried by the mask body and in communication with the server via a wireless link. The method may include operating a processor in each mask device to send an alert message to the server when the at least one contaminant concentration value respectively exceeds at least one threshold.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

This invention relates to an electronic device for monitoring the air quality intake/exhalation for a user. In addition, the device contains sensors for measuring vital health statistics to symptoms that result from exposure. Exposure can include but is not limited too infectious disease, containments in the local air, or specific chemicals that workers can be exposed to via occupation. In this sense, if a person painting a car is wearing a mask at a factory, there is still a need to limit a time duration of the person performing this task per day. Occupational hazards often include things like personal fatigue, or personal injury due to neglecting early symptoms.

The embodiments seek to decouple the sensor from static measurements and allow for dynamic measurements in systems where the response is not wide sense stationary allowing the end user to aggregate multiple data points or moments in summarizing the health of a larger population or work group. The sensor allows for remote monitoring of the smart snorkel by providing hooks into the internet of things (IoT) via cellular, Wi-Fi (i.e. IEEE 802.11 variants), and other leading radio links. The software suite provides a framework in which municipalities can rapidly implement and verify various safety points of the sensors in the digital transformation of legacy systems to include water treatment facilities, waste management, air quality control, and many other smart city initiatives.

In recent times, infectious diseases have gripped both our economies and local communities at a heightened sense due to globalization. Novel viruses have become increasingly dangerous to populations due to their spread via droplets from an infected person being spread to close contact. Outside of social distancing, persons are forced to wear masks with differing levels of filtration to block particulates, and in some cases no effective filtering at all. Regardless of the mask type, or face garment, there exists the need to monitor what a person is coming in contact with through this mask. There a numerous air quality sensors, thermal thermometers, and other vital measuring sensors in the market.

This invention is intended to improve tracking of garments worn by humans to block transmission of undesired particulates to their internal respiratory system. Due to the sensor being located on the face, we gather other inflection points like body temperature if the sensor is coupled appropriately. This is just amongst the few parameters we can track, and the goal is teaching a broader concept of using machine learning to detect distressed persons wearing the mask as result of exposure to these environmental contaminants.

The Smart Personal Quality Sensor provides a means for the end-user to remotely monitor the state of critical factor (s) such as, but not limited to: volatile organic compounds, dissolved oxygen, body temperature, intake humidity, and even airborne toxins like carbon monoxide. The state of the critical factors(s) is/are computed by the onboard firmware and then reported to the end-user via a wireless link.

The state of the aforementioned critical factors is ascertained in real-time using an on-board microprocessor, with onboard visible indicators, and a low energy wireless link database storage of the user data. The wireless link shall support Bluetooth Low Energy (BLE) communication protocol. The chosen antenna and radio frequency (RF) substrate are fully compatible with all competing lower-power standards/communication radios.

The Smart Personal Quality Sensor is powered by single, standard, commercially-available coin cell battery. The onboard firmware is optimized for minimal power consumption, allowing the Smart Personal Quality Sensor to be deployed for extended periods of time, in between multiple wash cycles of attached apparel (i.e. facemask). By the sensor being detachable in nature the user is not concerned with sensor damage and may keep the sensor long beyond the mask use, or carry over to a new mask.

The companion software application running on the remote, BLE-enabled device (e.g. smart phone, tablet, laptop, etc.) allows for a scalable framework of useful functions such as, but not limited to: customizable critical factor alert thresholds, customizable critical alert semaphores that can be raised on various communications channels (e.g. cellular short message service (SMS), Wi-Fi, SUB-1G etc.), low battery alerts, chemical compound expiration alerts, long-term critical factor data logging and analysis via IoT Cloud services, etc.

A network of multiple Smart Personal Quality Sensors can be deployed at various locations across a site, allowing for the remote monitoring of various points within a system whose critical factor(s) experience variations with respect to location. In contrast with typical technologies which involve invasive wired connections to be established throughout the site, the Smart Personal Quality Sensors affords the end-user increased surveilled coverage through a non-invasive, wireless link.

Figure 7:
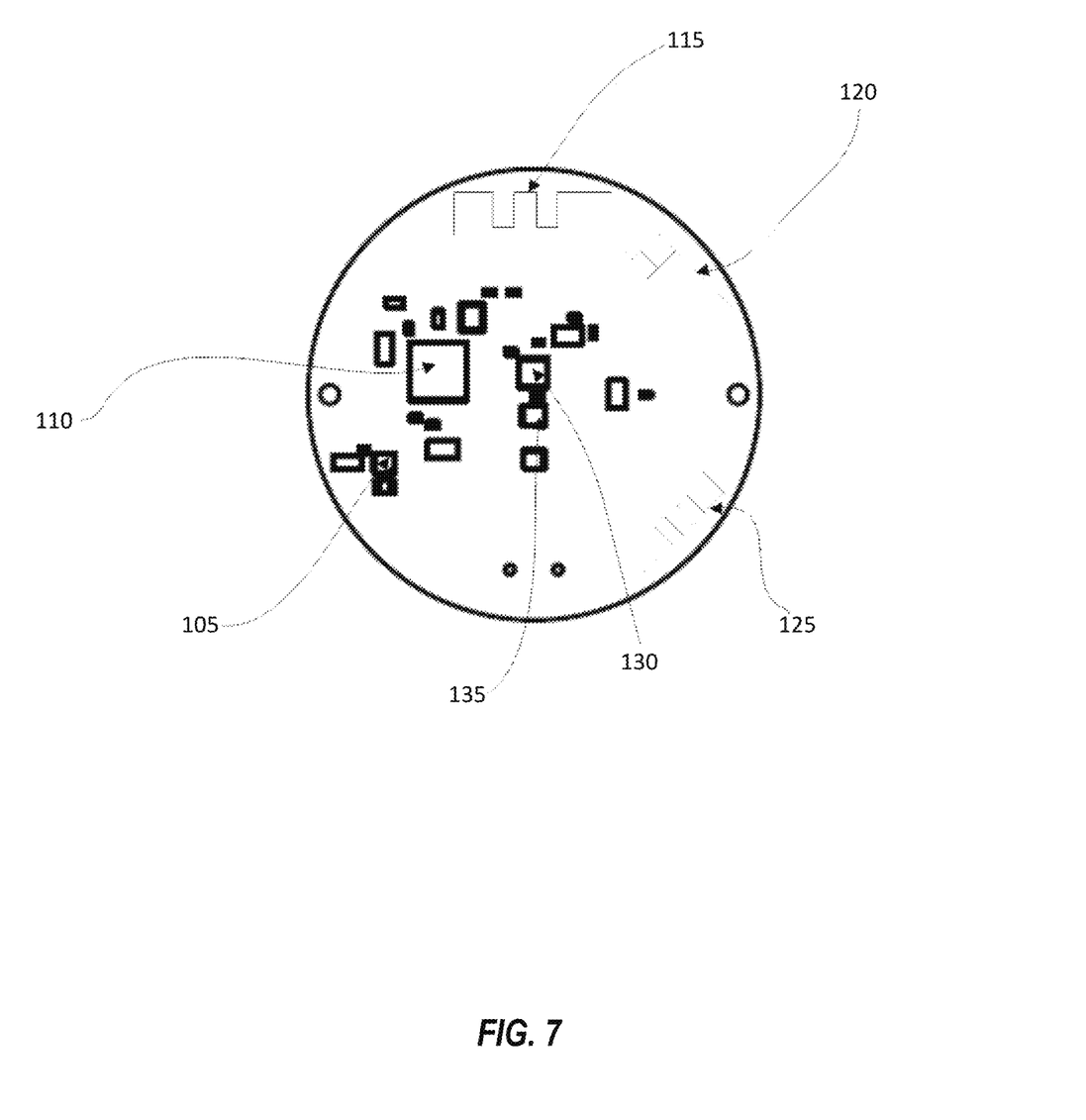
FIG. 7 is a schematic diagram of a circuit board from a mask device in a fifth embodiment of the monitoring system, according to the present invention.

Referring briefly to FIG. 7, the Smart Personal Quality Sensor printed circuit board 100 contains an on-board, BLE-compliant RF microcontroller (MCU) 110 equipped with an on-board PCB antenna 115. The MCU 110 interfaces with a number of co-located air quality sensors 135 via a digital, serial interface. The non-contact IR thermopile is used to measure skin temperature to check for fevers etc. The PCB comes equipped with an on-board voltage-regulation circuit 105 to utilize the entire coin cell battery current capacity. The onboard IMU is used to detect when the mask is worn, if the user is moving about their job in a normal fashion, and if the user coughs are performs any gestures that appears anomalous versus the larger group of mask wearers this is flagged in the software.

The software application layer is intended to devise a quality-of-life compliance system where a general color mapping interface for mapping N number of monitored events is mapped to an N number of numeric codes. The reactive sensor element is capable of changing its readout in response to the airborne chemical, as a reaction to a number of agents designed or engineered by the individual user. Several manufacturers will distribute the reactive sensors as add-ons.

The software application also includes a server side application that allows remote monitoring service providers to service the alerts for a large number of users and is definable to provide different alert triggers depending on user specific requests. These alerts can be programmed using our custom programming language and transferred remotely to the smart snorkel where the device now communicates with a local server near location or in a remote application using a cellular link.

The software application also includes a server side application that allows remote monitoring service providers to service the alerts for a large number of users and is definable to provide different alert triggers depending on user specific requests. These alerts can be programmed using our custom programming language and transferred remotely to the smart snorkel where the device now communicates with a local server near location or in a remote application using a cellular link.

This invention relates to an electronic device for monitoring the air quality intake/exhalation for a user. In addition, the device contains sensors for relating vital health statistics and the symptoms that result from exposure. Exposure can include but is not limited too infectious disease, containments in the local air, or specific chemicals that workers can be exposed to via occupation. In this sense, if a person painting a car is wearing a mask at a factory, there is still a need to limit hours and duration of the person performing this task per day. Occupational hazards often include things like personal fatigue, or personal injury due to neglecting early symptoms. The embodiments seek to decouple the sensor from static measurements and allow for dynamic measurements in systems where the response is not wide sense stationary allowing the end user to aggregate multiple data points or moments in summarizing the health of a larger population or work group. The sensor allows for remote monitoring of the smart snorkel by providing hooks into the IoT via cellular, Wi-Fi, and other leading radio links. The software suite provides a framework in which municipalities can rapidly implement and verify various safety points of the aforementioned sensors in the digital transformation of legacy systems to include water treatment facilities, waste management, air quality control, and many other smart city initiatives.

A detachable snorkel wherein airborne contaminates are mapped to alerts and indicators as defined by user selectable parameters to include: the presence of gas and chemicals as it translates to being inhaled/exhaled by the human through a facemask; on alert, provide the ability to assign decrees to criticality and user selectable priorities on notifications; to allow for user selectable scan intervals where an increase/decrease of scan interval is capable depending on concentration levels (i.e. PPM), or particulate type (P2.5); the ability to beacon both raw sensor values in additional to user defined reaction thresholds when multiple sensor inputs cross user defined thresholds by broadcasting over radio frequencies; and the ability to provide lock out codes to prevent tampering with alerts where individual may seek to circumvent compliance.

In some embodiments, where a VOC sensor, carbon dioxide sensor, and other air quality sensors are configured to read contaminants continuously and periodically as defined by the user through software. In some embodiments, where the smart air quality sensor is attached to facial mask for protection against airborne contaminants. In some embodiments, where an IMU is used for cough detection in monitored person. In some embodiments, where a non-contact IR thermopile is used to measure body temperature through the apparel. In some embodiments, wherein the sensor can ascertain report distance from other masks as reported over the cloud. In some embodiments, the device has the ability to wall mount and detect air quality changes on adjacent surfaces, or provide point source monitoring of items (i.e. kitchen stoves, furnaces) that are prone to leaks of toxic gases. In some embodiments, the device may include a wireless beacon directed to a companion radio transceiver for system alerts.

Figure 1:
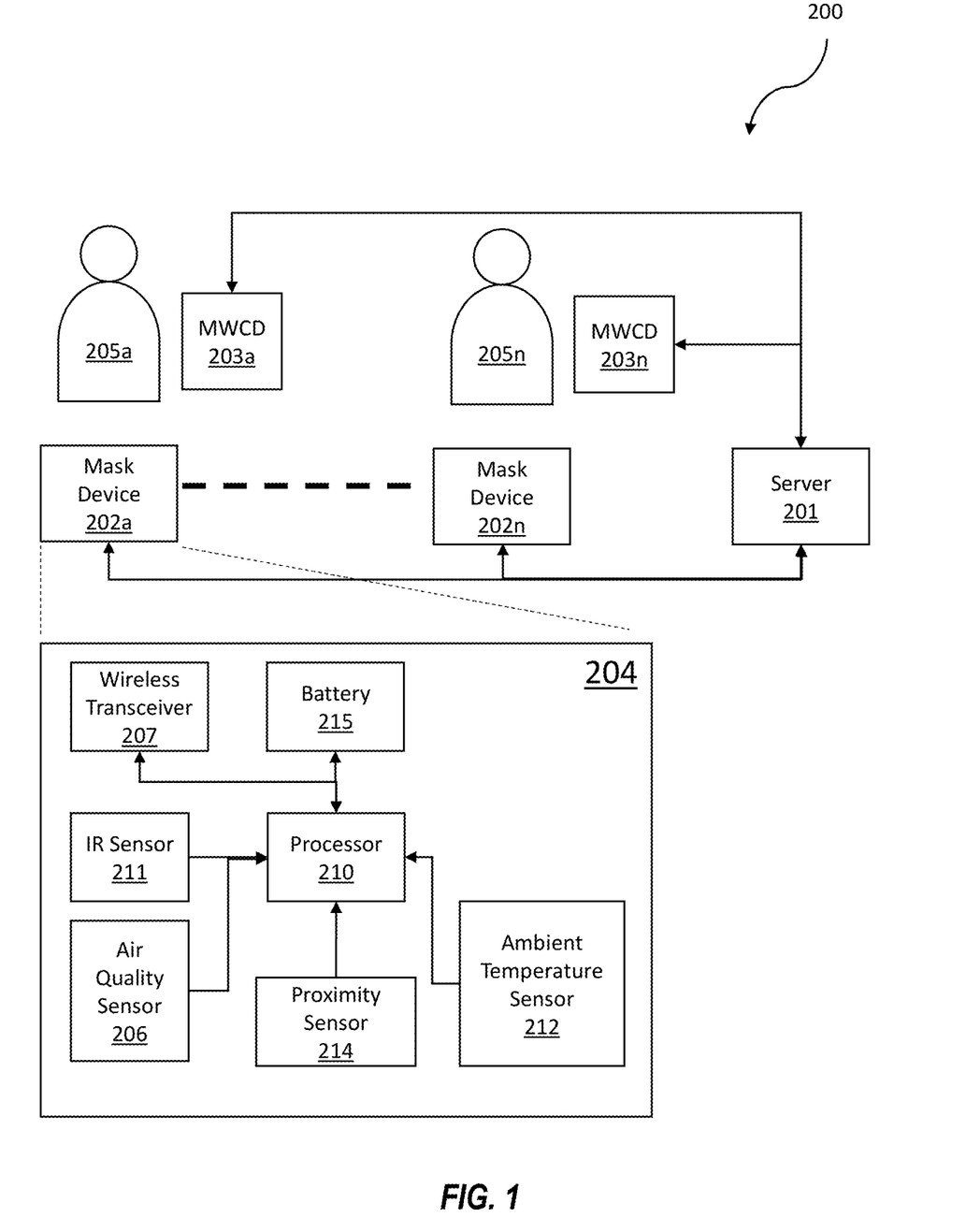
FIG. 1 is a schematic diagram of a first embodiment of a monitoring system, according to the present invention.
Figure 2:
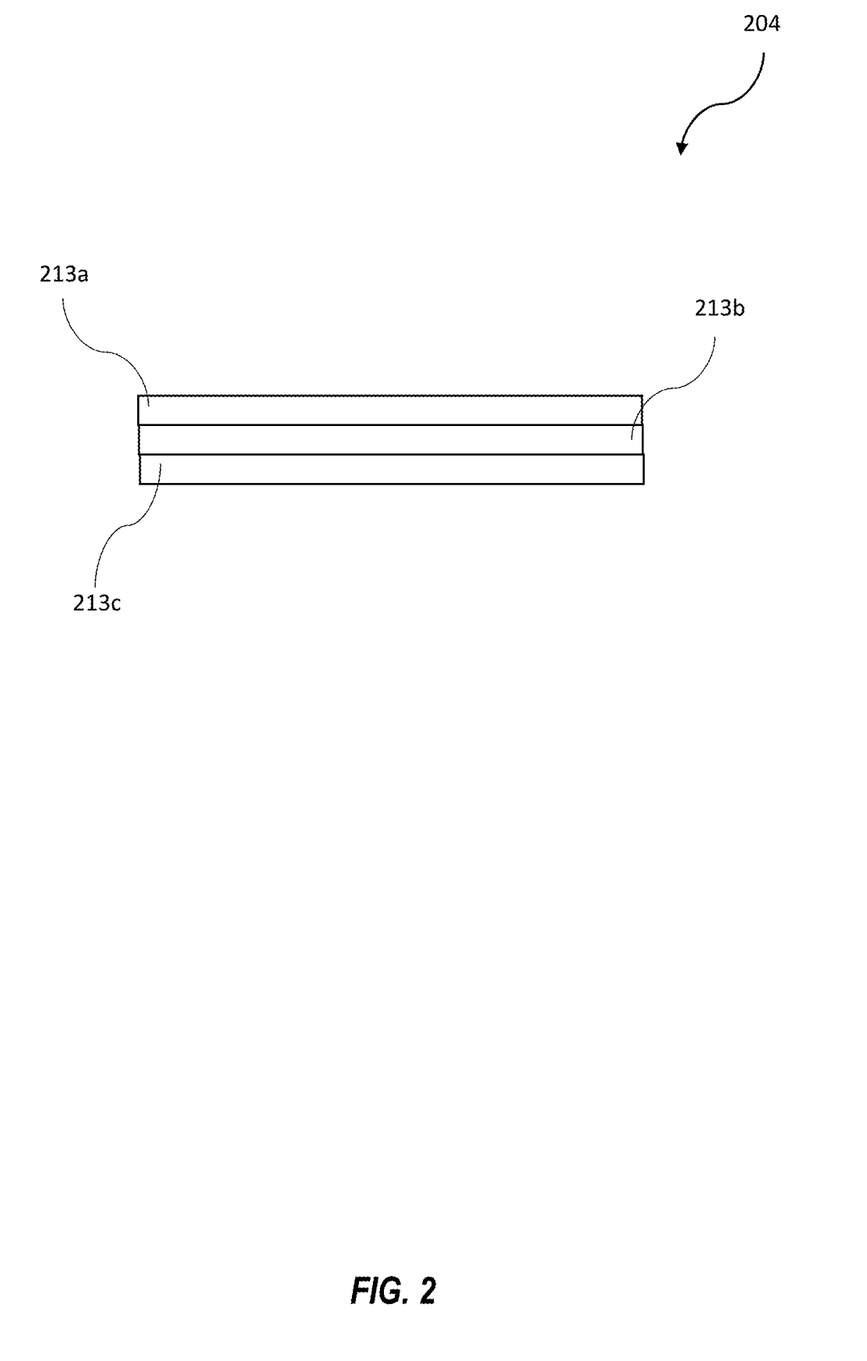
FIG. 2 is a schematic cross-sectional view of the mask body from the mask device of the monitoring system of FIG. 1.

Referring now to FIGS. 1-2, a monitoring system 200 according to the present disclosure is now described. The monitoring system 200 illustratively includes a server 201 (e.g. a standalone computing device or a cloud computing platform), and a plurality of mask devices 202a-202n in communication with the server. Additionally, the monitoring system 200 illustratively includes a plurality of mobile devices 203a-203n (e.g. cellular device, tablet computing device, laptop computing device) in communication with the server 201 and respectively associated with the plurality of mask devices 202a-202n.

Each mask device 202a-202n includes a mask body 204 to be worn by a respective user 205a-205n, and an air quality sensor 206 carried by the mask body and configured to detect a plurality of contaminant concentration values in air breathed through the mask body. The air quality sensor 206 is configured to detect the plurality of contaminant concentration values comprising a carbon dioxide concentration value, and a VOC concentration value, for example.

In some embodiments (FIGS. 3-4), the air quality sensor 206 is positioned to sample ambient air. In other embodiments, the mask device 202a-202n may comprise a respirator form factor with filtered air intake, and the air quality sensor 206 is positioned upstream of the filtered air intake.

Each mask device 202a-202n includes a wireless transceiver 207 carried by the mask body 204 and in communication with the server 201 via a wireless link. In some embodiments, the wireless link is via the respective mobile device 203a-203n, and the wireless transceiver 207 may comprise a BLE transceiver, or a ZigBee transceiver communicating with the respective mobile device. In other embodiments, the wireless link is direct, and the wireless transceiver 207 may comprise a cellular transceiver, for example.

Each mask device 202a-202n illustratively comprises a processor 210 carried by the mask body 204 and coupled to the air quality sensor 206 and the wireless transceiver 207. The processor 210 is configured to send an alert message to the server 201 when one or more of the plurality of contaminant concentration values respectively exceeds a corresponding plurality of thresholds. The server 201 is configured to forward the alert message to the respective mobile device 203a-203n to alert a respective user 205a-205n.

Each mask device 202a-202n illustratively includes an IR sensor 211 carried by the mask body 204 and coupled to the processor 210. The IR sensor 211 is configured to detect a body temperature of the respective user 205a-205n. Each mask device 202a-202n illustratively comprises an ambient temperature sensor 212 carried by the mask body 204 and coupled to the processor 210. The ambient temperature sensor 212 is configured to detect an ambient temperature (i.e. the temperature of the air surrounding the respective user 205a-205n).

In some embodiments, each mask device 202a-202n includes an inertial measurement unit (IMU). The processor 210 is configured to cooperate with the IMU to detect one or more of a cough event of the respective user 205a-205n, a sneeze event of the respective user, a breathing event of the respective user, and a fall event of the respective user. In particular, the processor 210 is configured to detect the cough or sneeze event when the IMU indicates a movement to exceeds a movement threshold within a short time period (e.g. 0.5 seconds). Also, the processor 210 is configured to detect the breathing event when the IMU indicates periodic movement. The processor 210 is configured to detect the fall event when the IMU indicates abrupt movement and high force impact.

The mask body 204 illustratively comprises a plurality of layers 213a-213c. The plurality of layers 213a-213c comprises a submicron bio barrier layer. Each mask device 202a-202n illustratively includes a proximity sensor 214 carried by the mask body 204, and coupled the processor 210. The proximity sensor 214 is configured to detect when the mask body 204 is worn by the respective user 205a-205n. In some embodiments, each mask device 202a-202n may include an optical detector (i.e. in alternative or in addition to the proximity sensor 214) to detect when the mask body 204 is worn by the respective user 205a-205n.

Each mask device 202a-202n illustratively includes a battery 215 coupled the air quality sensor 206, the wireless transceiver 207, and the processor 210. The battery 215 may comprise a rechargeable battery, and each mask device 202a-202n may comprise a charging port coupled to the rechargeable battery.

Another aspect is directed to a method of operating a monitoring system 200 comprising a server 201, and a plurality of mask devices 202a-202n in communication with the server. Each mask device 202a-202n comprises a mask body 204 to be worn by a respective user 205a-205n, an air quality sensor 206 carried by the mask body and configured to detect at least one contaminant concentration value in air breathed through the mask body, and a wireless transceiver 207 carried by the mask body and in communication with the server 201 via a wireless link. The method may include operating a processor 210 in each mask device 202a-202n to send an alert message to the server 201 when the at least one contaminant concentration value respectively exceeds at least one threshold.

Figure 8A:
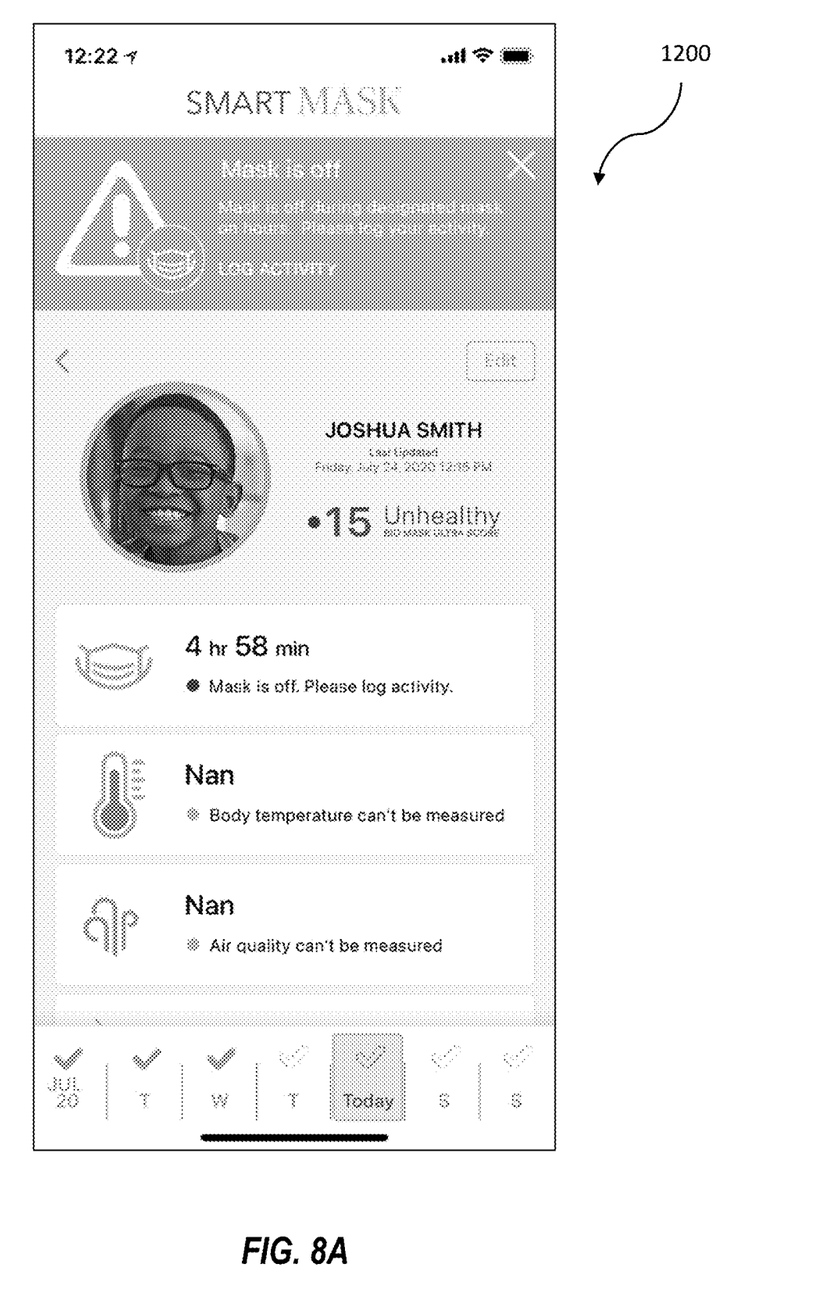
FIGS. 8A-8C are screenshots of a user interface from a mobile device in a sixth embodiment of the monitoring system, according to the present invention.
Figure 8B:
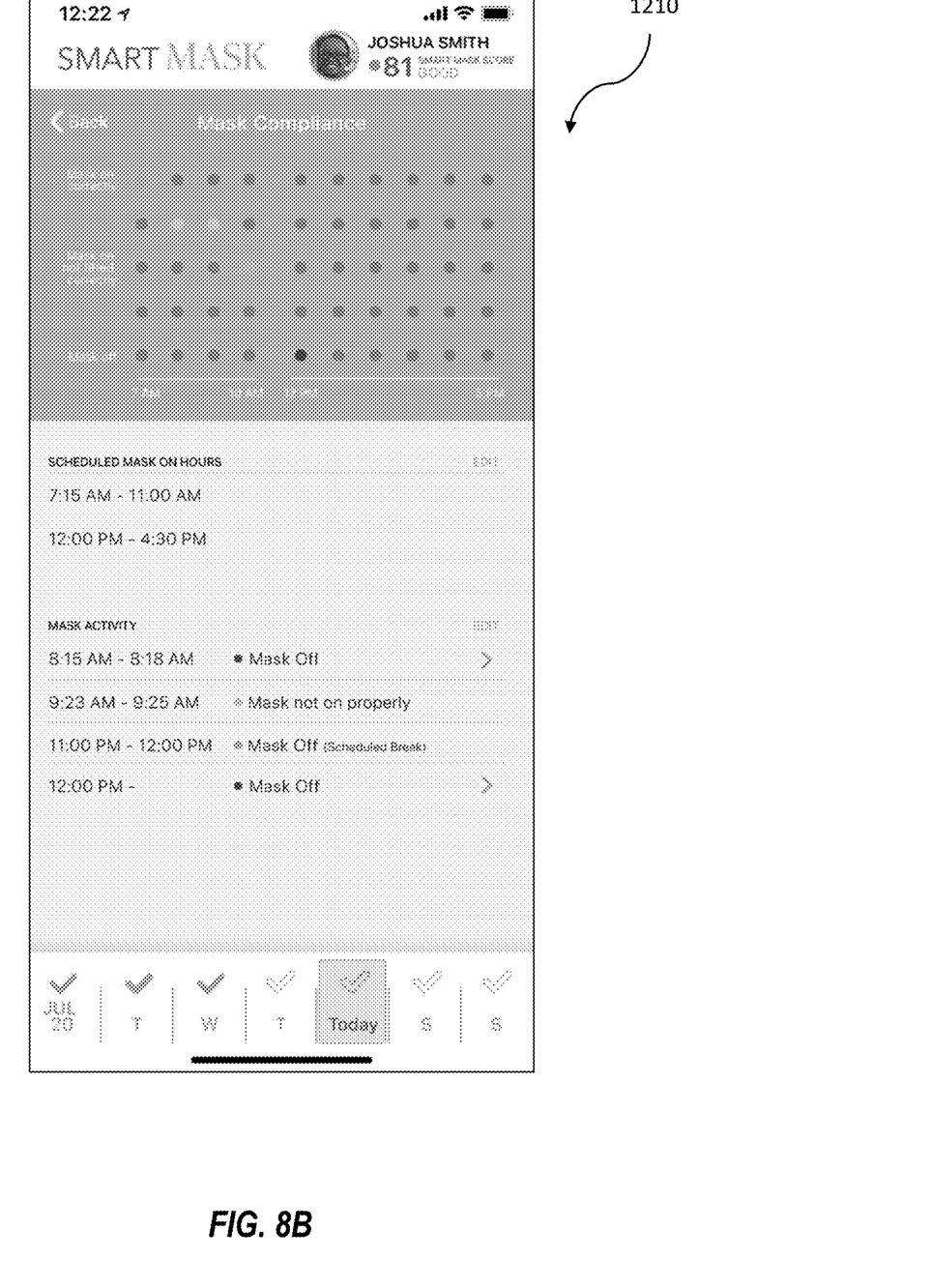
Figure 8C:
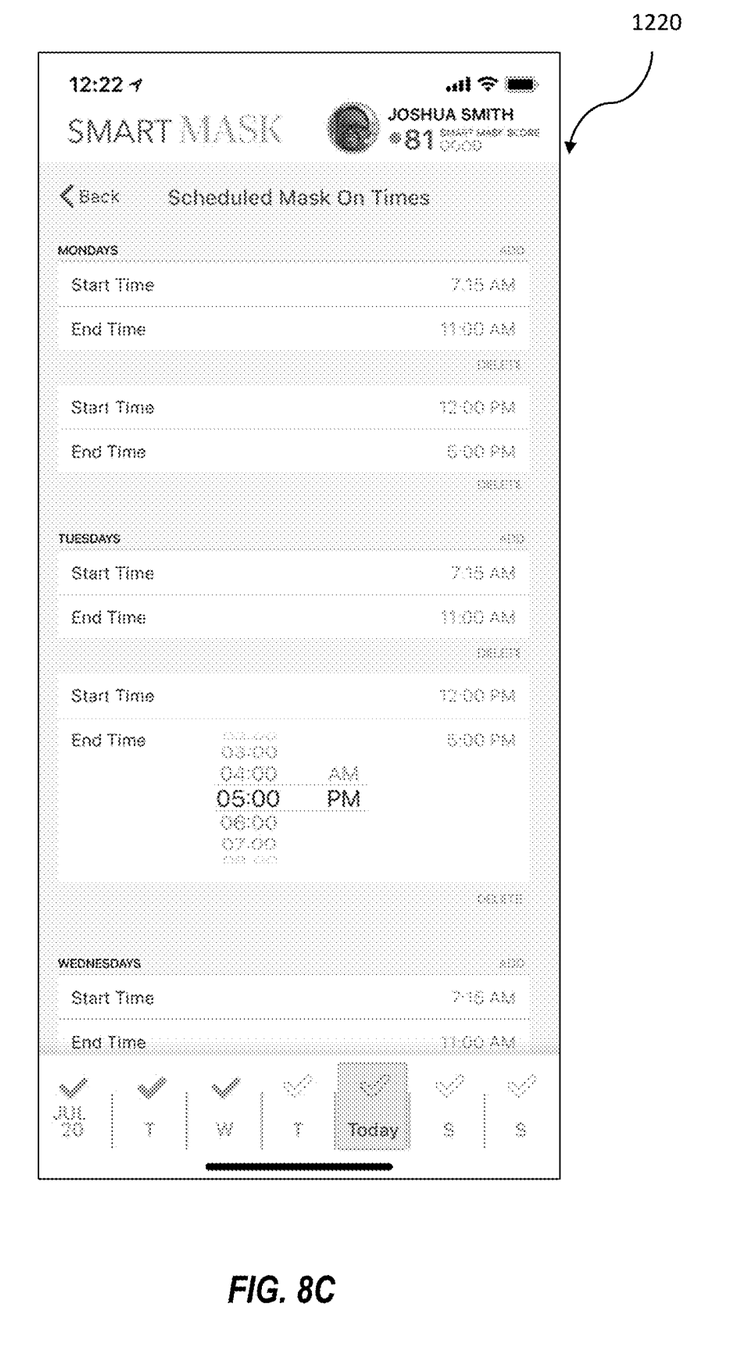

Referring now briefly to screenshots 1200, 1210, 1220 of FIGS. 8A-8C, the processor 210 is configured to generate alert messages, which are directed to the server 201. In this monitoring system 200, the server 201 is receiving alert messages from a large number of devices, and processing them for display within an administrative interface. The server 201 is also configured to forward the alert messages to the user interface of the respective mobile device 203a-203n, as shown in each of the screenshots 1200, 1210, 1220. As noted above, the processor 210 is configured to perform data fusion on a plurality of data sources (i.e. sensor output). The thresholds for generating alerts may be system wide and set in the administrative interface or locally controlled via the user interface. For example, if a user fails to wear the respective mask device 202a-202n when expected (i.e. during working hours), the processor would generate the alert message, as shown in the screenshots 1210, 1220.

In the screenshot 1200, the user interface illustratively includes a notification interface on the top, and a current status interface on the bottom. The notification interface illustratively includes a current alert message. The current status interface comprises an indication of current state (e.g. the illustrated unhealthy), an indication of the current sensor output, and a current date.

In the screenshot 1210, the user interface illustratively includes a time history of mask compliance for the respective user 205a-205n. In the screenshot 1220, the user interface illustratively includes a scheduling interface for the respective user 205a-205n to note when the mask device should be worn. Advantageously, the monitoring system 200 may increase mask wearing compliance among the plurality of users 205a-205n. Moreover, the monitoring system 200 provides alert messages to nudge plurality of users 205a-205n into improved compliance, and also monitors the health statistics of the plurality of users.

Figure 3:
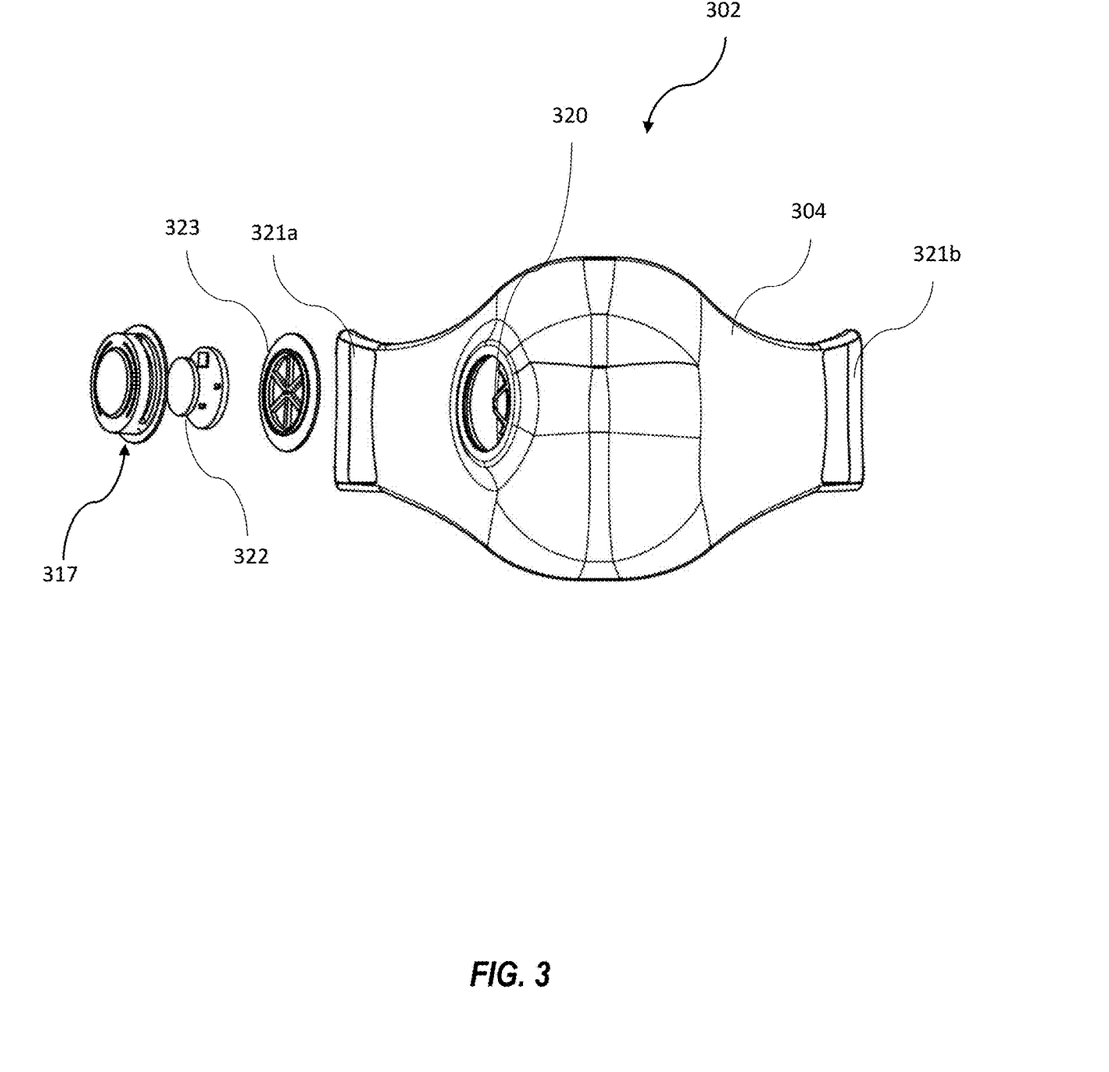
FIG. 3 is a schematic exploded view of the mask device from a second embodiment of the monitoring system, according to the present invention.
Figure 4:
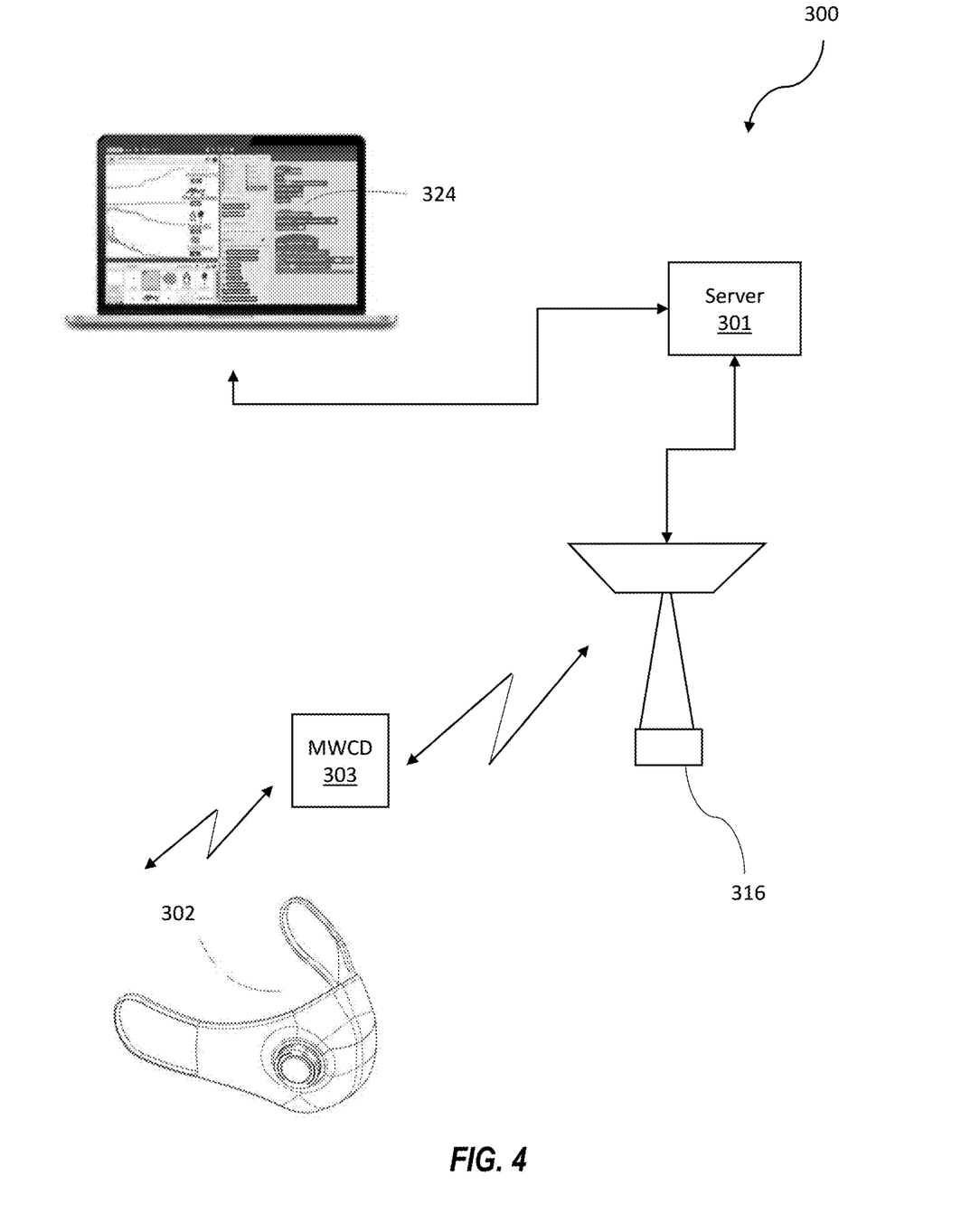
FIG. 4 is a schematic diagram of the second embodiment of the monitoring system.

Referring now additionally to FIGS. 3-4, another embodiment of the monitoring system 300 is now described. In this embodiment of the monitoring system 300, those elements already discussed above with respect to FIGS. 1-2 are incremented by 100 and most require no further discussion herein. This embodiment differs from the previous embodiment in that this monitoring system 300 illustratively includes mask device 302 having an ear loop style mask body 304. The mask body 304 illustratively comprises first and second ear loops 321a-321b for latching onto the respective user. Of course, in some embodiments, the mask body 304 may comprise one or more head straps coupled to the first and second ear loops 321a-321b.

The mask device 302 illustratively includes a cover 317, an electronic device 322, a carrier housing 323 receiving the electronic device, and a port 320 receiving the carrier housing. As will be appreciated, the respective user breaths air through the intake port. The cover 317 is to protect the port from external damage. The electronic device 322 may comprise a circuit board carrying the electronic devices of the mask device 302 (i.e. the wireless transceiver, the battery, processor, the IR sensor, the air quality sensor, the proximity sensor, and the temperature sensor of the embodiments of FIGS. 1-2).

In this embodiment, only a single mobile device 303 and mask device 302 are shown for illustrative clarity. Here, the monitoring system 300 illustratively comprises a base station 316 in communication with the mobile device 303, and the mobile device is in communication with the mask device 302. The monitoring system illustratively includes an administrative device 324 configured to receive data from the server 301.

Figure 5:
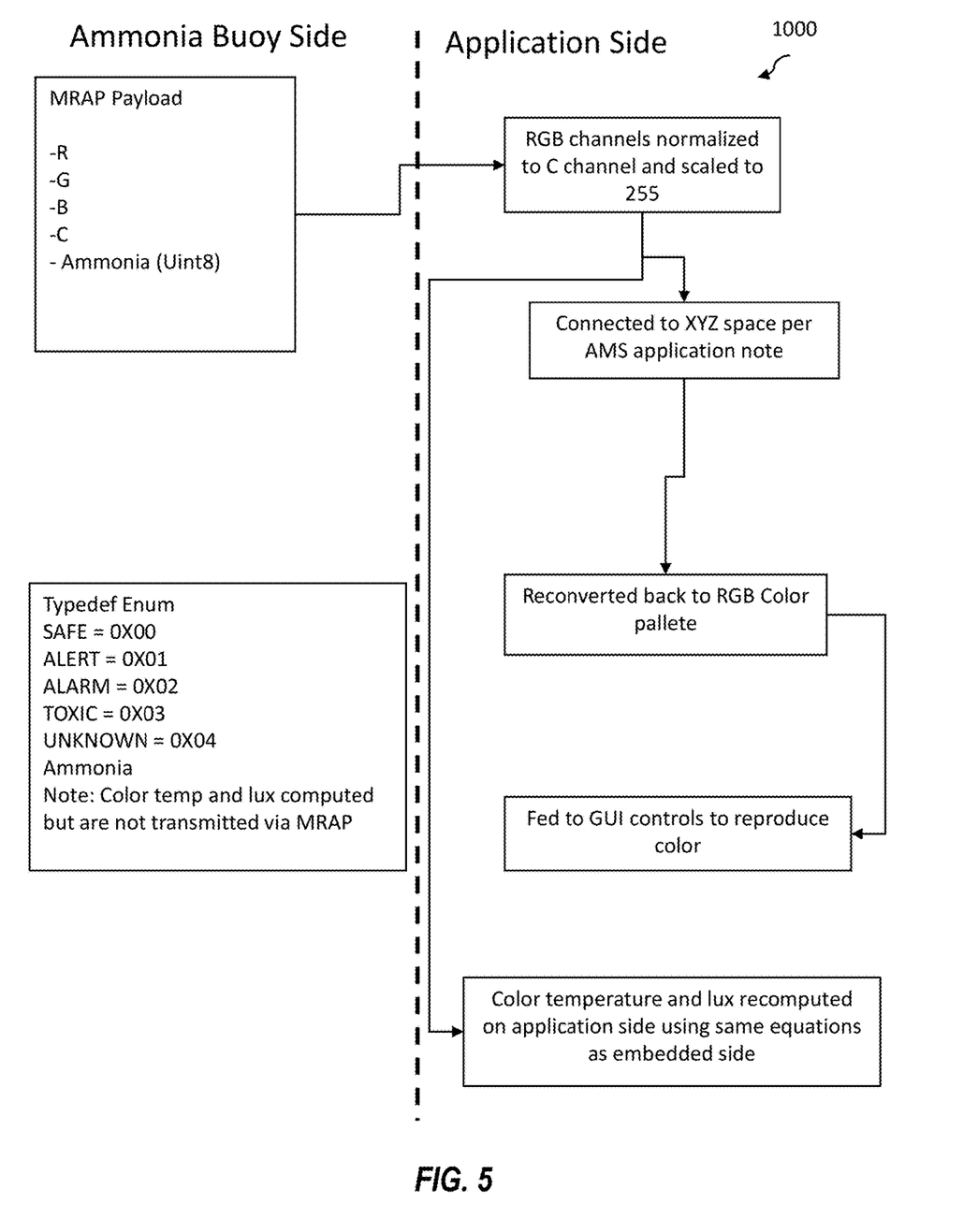
FIG. 5 is a flow diagram of operation within a third embodiment of the monitoring system, according to the present invention.
Figure 6:
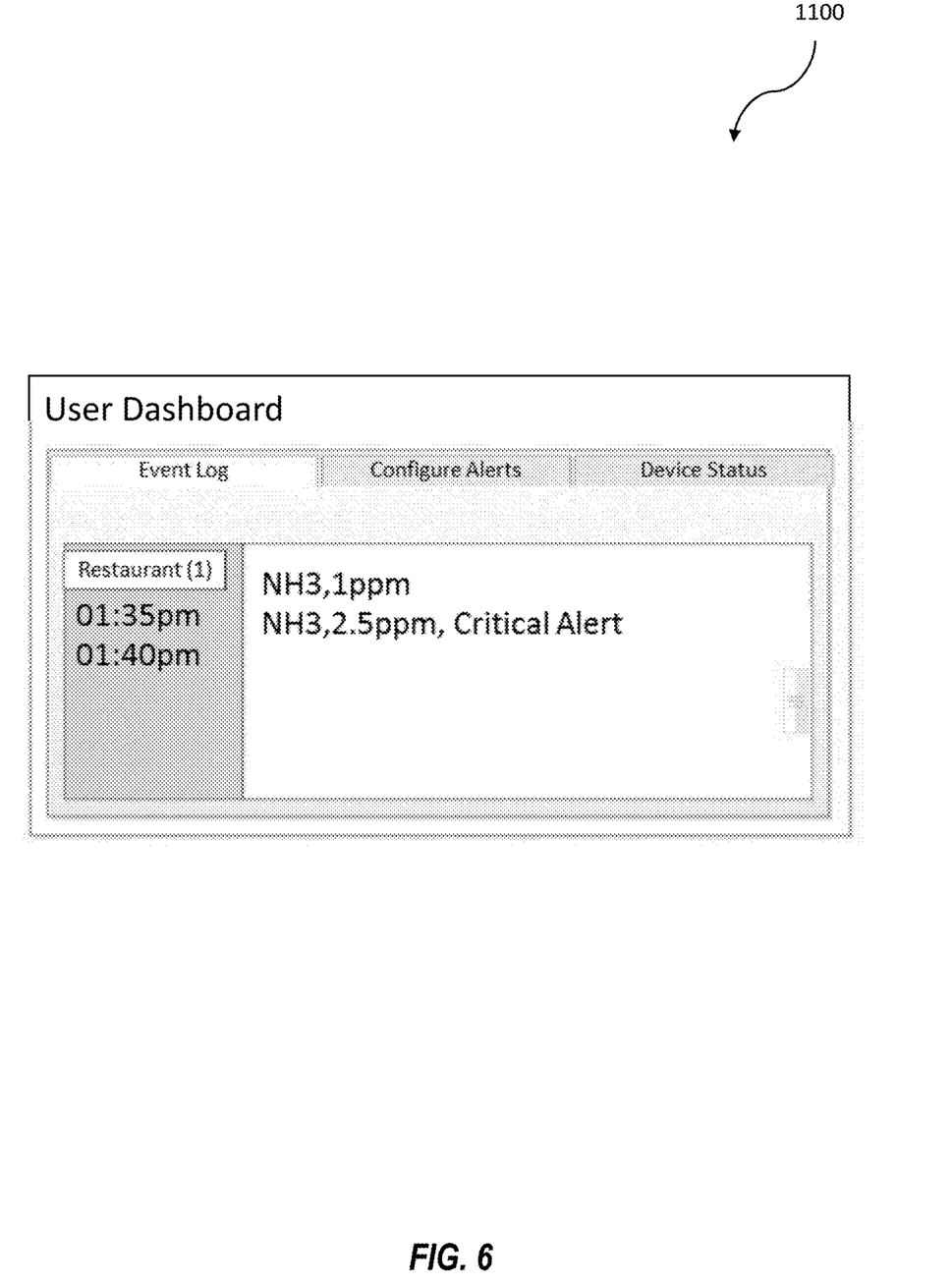
FIG. 6 is a diagram of a user interface within a fourth embodiment of the monitoring system, according to the present invention.

Referring now to FIGS. 5-6, a diagram 1000 shows data flow within an example embodiment of the monitoring system 200, 300. A diagram 1100 illustrates an example embodiment of a user interface for the administrative device 324. The user interface illustratively includes a tabbed interface with an event log tab, an alert configuration tab, and a device status tab.

Figure 9A:
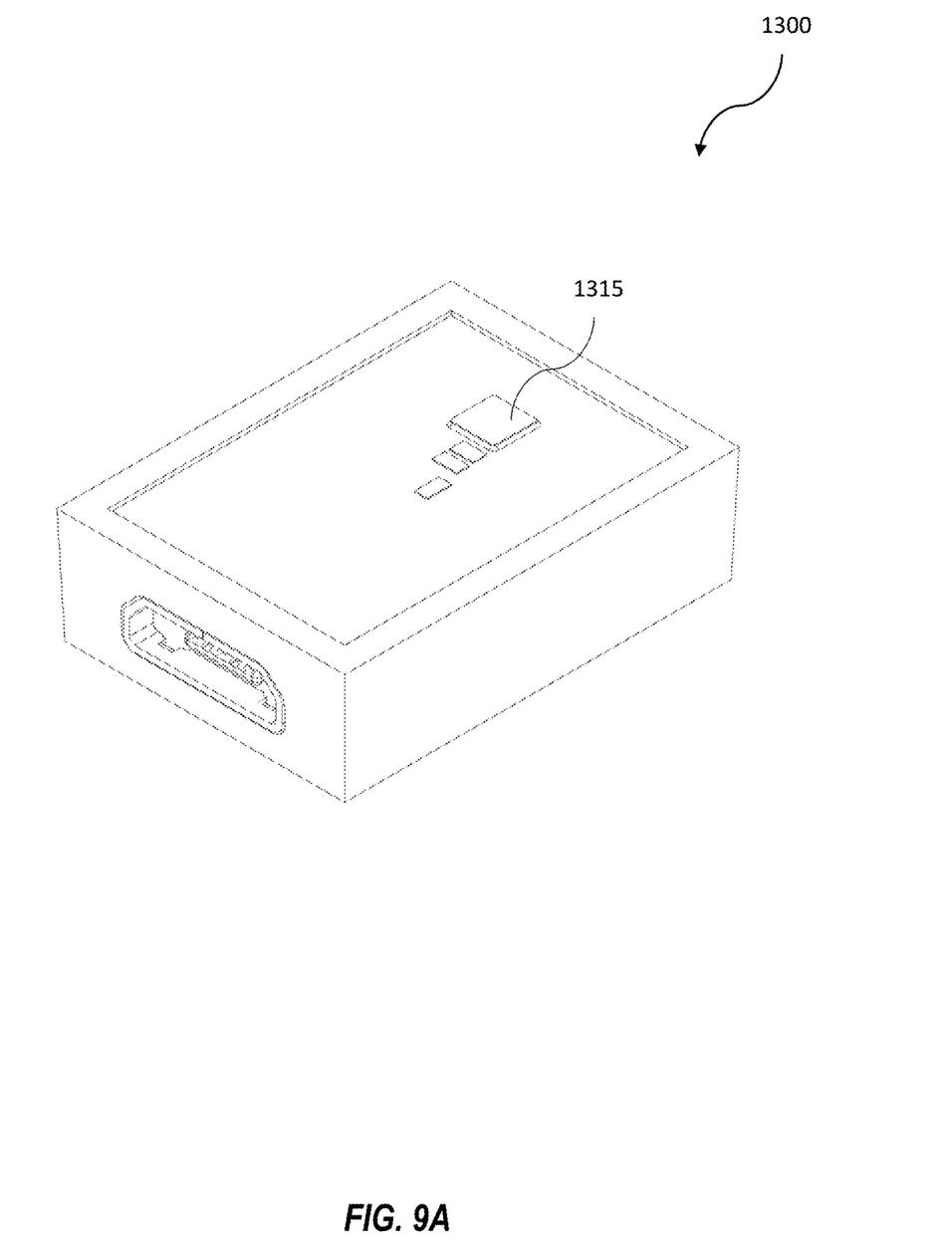
FIGS. 9A-9C are schematic diagrams of a seventh embodiment of the monitoring system, according to the present invention.
Figure 9B:
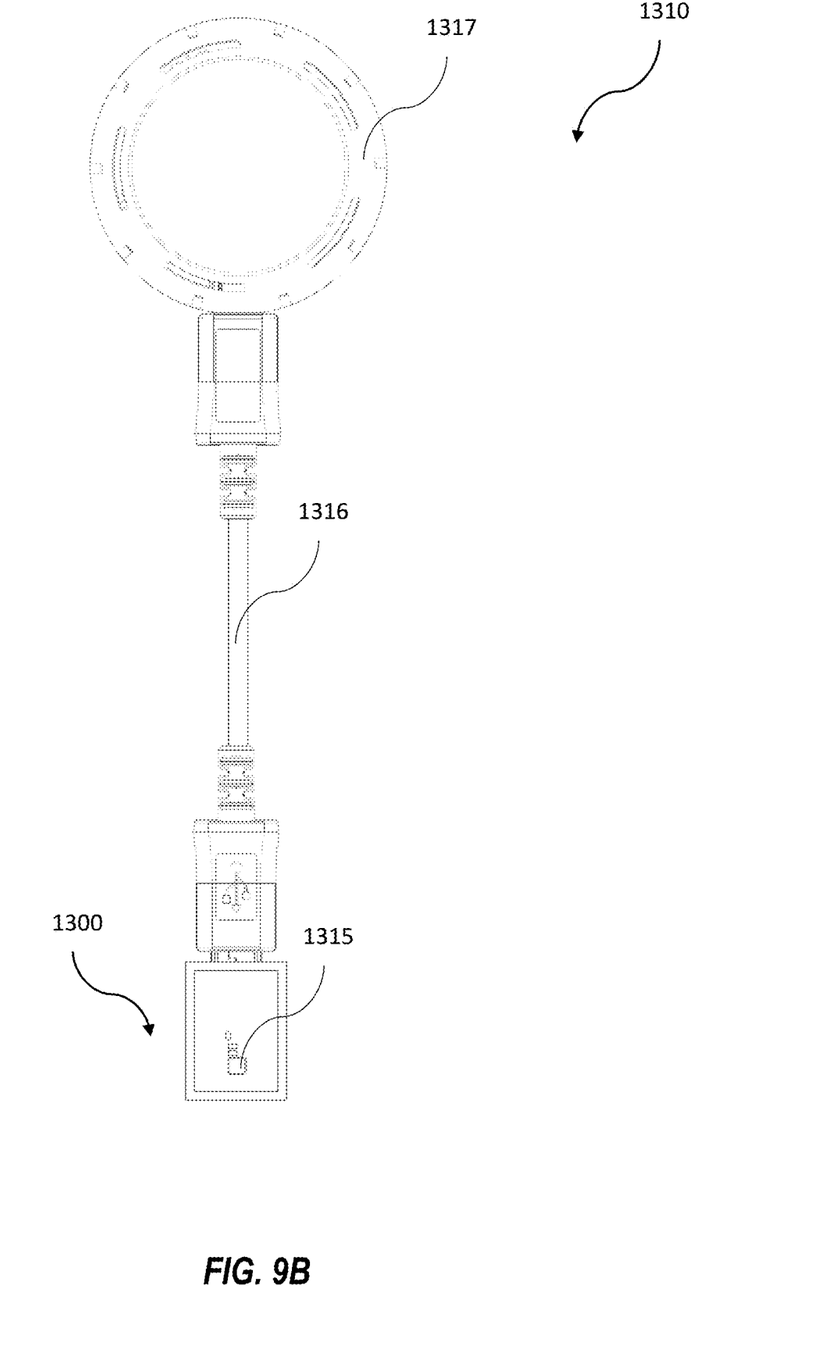
Figure 9C:
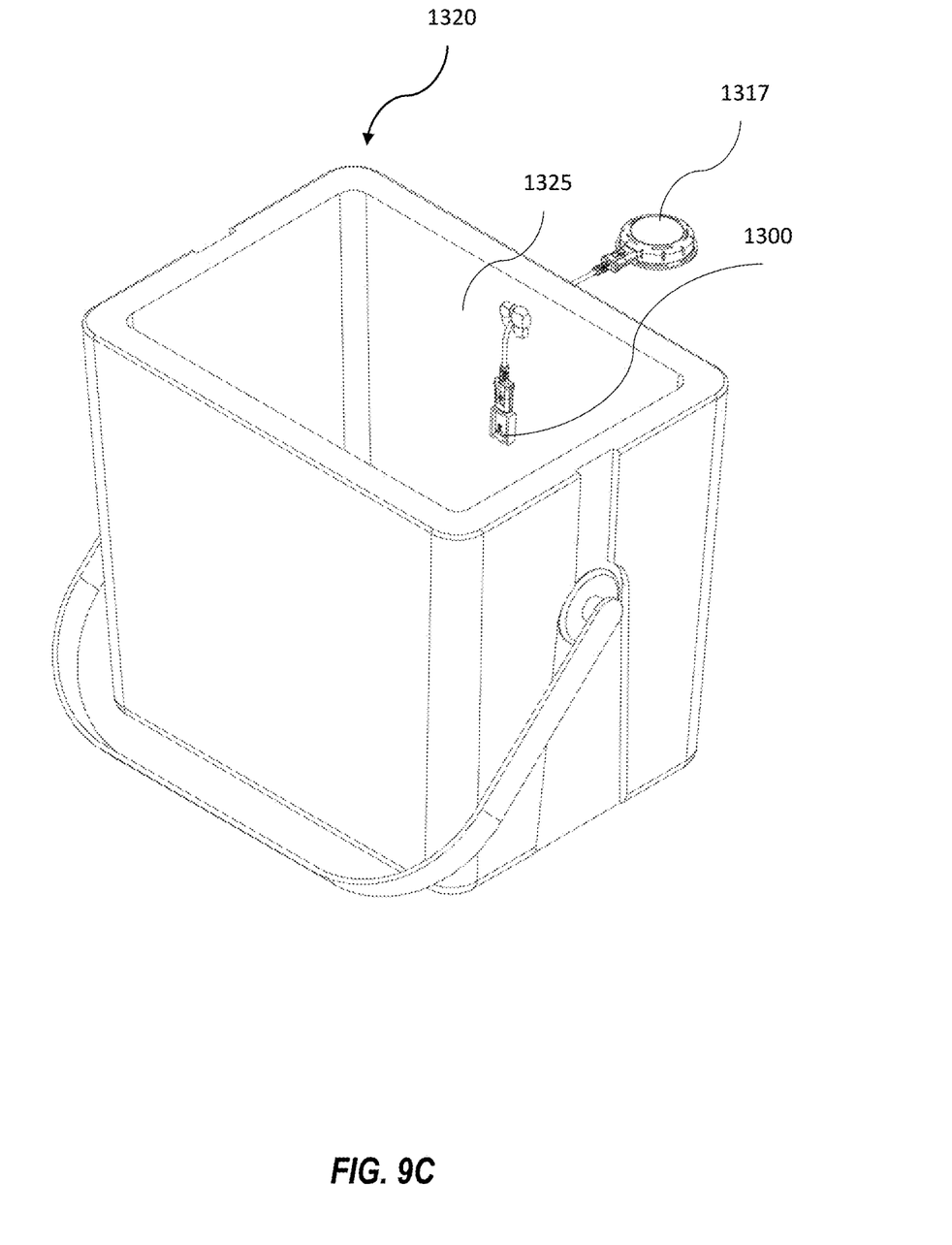

Referring now to FIGS. 9A-9C, another embodiment 1300, 1310, 1320 of an example embodiment of the monitoring system is now described. Here, there is an improved design to monitor for hazards conditions in a mobile cold storage container 1320 where an add-on sensor called a cold finger 1300 measures internal temperatures by way of being affixed to a wall/surface 1325 inside the container. There is a need to monitor temperatures as low as −70° F. for Vaccines that are stored in dry ice. The temperature is beyond the operating range of most commercially available electronics. In this embodiment 1310, the cold finger is attached to the snorkel via a cable 1316 where the snorkel 1317 is mounted outside the cooler versus the cold finger internal to the cooler. The thermocouple 1315 can realize the extreme temperate whereas the RF circuitry is protected from exposure. On the application side 1000, there is a need to know how long the contents were exposed to untoward environments like exhaust exposure from planes and trucks as the sensitive goods boards and disembarks along the supply chain.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

The invention claimed is:

1. A monitoring system comprising:
a server; and
a plurality of half-mask mask devices in communication with said server, each half-mask mask device comprising
a mask body to be worn by a respective user and comprising a port,
a carrier housing carried by the mask body in the port,
a circuit board carried by the carrier housing,
an air quality sensor carried by said circuit board and configured to detect at least one contaminant concentration value in air breathed through said mask body,
a wireless transceiver carried by said circuit board and in communication with said server via a wireless link,
an inertial measurement unit (IMU) carried by said circuit board, and
a processor carried by said circuit board and coupled to said air quality sensor, said wireless transceiver, and said IMU, said processor configured to
send an alert message to said server when the at least one contaminant concentration value respectively exceeds at least one threshold, and
detect a cough event of the respective user, and a sneeze event of the respective user based upon said IMU indicating a movement exceeding a movement threshold within a time period.

2. The monitoring system of claim 1 wherein each half-mask mask device comprises an infrared (IR) sensor carried by said circuit board and coupled to said processor, said IR sensor configured to detect a body temperature of the respective user.

3. The monitoring system of claim 1 wherein each half-mask mask device comprises an ambient temperature sensor carried by said circuit board and coupled to said processor, said ambient temperature sensor configured to detect an ambient temperature.

4. The monitoring system of claim 1 wherein said processor is configured to detect at least one of a breathing event of the respective user and a fall event of the respective user.

5. The monitoring system of claim 1 wherein said air quality sensor is configured to detect a plurality of contaminant concentration values.

6. The monitoring system of claim 5 wherein said air quality sensor is configured to detect the plurality of contaminant concentration values comprising a carbon dioxide concentration value, and a Volatile Organic Compound (VOC) concentration value.

7. The monitoring system of claim 1 wherein said mask body comprises a plurality of layers, said plurality of layers comprising a submicron bio barrier layer.

8. The monitoring system of claim 1 wherein each half-mask mask device comprises a proximity sensor carried by said circuit board, and coupled said processor, said proximity sensor configured to detect when said mask body is worn by the respective user.

9. The monitoring system of claim 1 wherein each half-mask mask device comprises a battery coupled to said air quality sensor, said wireless transceiver, and said processor.

10. The monitoring system of claim 1 further comprising a plurality of mobile devices in communication with said server and respectively associated with said plurality of half-mask mask devices; and wherein said server is configured to forward the alert message to a respective mobile device.

11. A monitoring system comprising:
a server;
a plurality of half-mask mask devices in communication with said server, each half-mask mask device comprising
a mask body to be worn by a respective user and comprising a port,
a carrier housing carried by the mask body in the port,
a circuit board carried by the carrier housing,
an air quality sensor carried by said circuit board and configured to detect a plurality of contaminant concentration values in air breathed through said mask body,
a wireless transceiver carried by said circuit board and in communication with said server via a wireless link,
an inertial measurement unit (IMU),
an infrared (IR) sensor carried by said circuit board and configured to detect a body temperature of the respective user, and
a processor carried by said circuit board and coupled to said air quality sensor, said wireless transceiver, said IR sensor, and said IMU, said processor configured to send an alert message to said server when at least one of the plurality of contaminant concentration values respectively exceeds at least one threshold, and detect a cough event of the respective user, and a sneeze event of the respective user based upon said IMU indicating a movement exceeding a movement threshold within a time period; and a plurality of mobile devices in communication with said server and respectively associated with said plurality of half-mask mask devices, said server is configured to forward the alert message to said a respective mobile device.

12. The monitoring system of claim 11 wherein each half-mask mask device comprises an ambient temperature sensor carried by said circuit board and coupled to said processor, said ambient temperature sensor configured to detect an ambient temperature.

13. The monitoring system of claim 11 wherein said processor is configured to detect at least one of a breathing event of the respective user and a fall event of the respective user.

14. The monitoring system of claim 11 wherein said air quality sensor is configured to detect the plurality of contaminant concentration values comprising a carbon dioxide concentration value, and a Volatile Organic Compound (VOC) concentration value.

15. The monitoring system of claim 11 wherein said mask body comprises a plurality of layers, said plurality of layers comprising a submicron bio barrier layer.

16. The monitoring system of claim 11 wherein each half-mask mask device comprises a proximity sensor carried by said circuit board, and coupled said processor, said proximity sensor configured to detect when said mask body is worn by the respective user.

17. The monitoring system of claim 11 wherein each half-mask mask device comprises a battery coupled said air quality sensor, said wireless transceiver, and said processor.

18. A method of operating a monitoring system comprising a server, and a plurality of half-mask mask devices in communication with the server, each half-mask mask device comprising a mask body to be worn by a respective user and comprising a port, a carrier housing carried by the mask body in the port, a circuit board carried by the carrier housing, an air quality sensor carried by the circuit board and configured to detect at least one contaminant concentration value in air breathed through the mask body, a wireless transceiver carried by the circuit board and in communication with the server via a wireless link, and an inertial measurement unit (IMU), the method comprising:
operating a processor in each half-mask mask device to send an alert message to the server when the at least one contaminant concentration value respectively exceeds at least one threshold, and to detect a cough event of the respective user, and a sneeze event of the respective user based upon the IMU indicating a movement exceeding a movement threshold within a time period.

19. The method of claim 18 wherein each half-mask mask device comprises an infrared (IR) sensor carried by the circuit board and coupled to the processor; and further comprising operating the IR sensor to detect a body temperature of the respective user.

20. The method of claim 18 wherein each half-mask mask device comprises an ambient temperature sensor carried by the circuit board and coupled to the processor; and further comprising operating the ambient temperature sensor to detect an ambient temperature.

* * * * *